(12) United States Patent
Tan et al.

(10) Patent No.: US 6,350,453 B1
(45) Date of Patent: Feb. 26, 2002

(54) **TOCOTRIENOLS AND GERANYLGERANIOL FROM *BIXA ORELLANA* BYPRODUCTS**

(75) Inventors: Barrie Tan, Amherst; John Foley, Sunderland, both of MA (US)

(73) Assignee: American River Nutrition, Inc., Hadley, MA (US)

( * ) Notice: Subject to any disclaimer, the term of this patent is extended or adjusted under 35 U.S.C. 154(b) by 0 days.

(21) Appl. No.: 09/577,086

(22) Filed: May 24, 2000

Related U.S. Application Data

(60) Provisional application No. 60/135,463, filed on May 24, 1999.

(51) Int. Cl.$^7$ .............................................. A61K 35/78
(52) U.S. Cl. ..................... 424/195.1; 549/407; 549/408
(58) Field of Search ................................. 549/408, 407; 424/195.1

(56) References Cited

U.S. PATENT DOCUMENTS

| | | | |
|---|---|---|---|
| 2,486,541 A | 11/1949 | Baxter et al. | 260/333 |
| 4,603,142 A | 7/1986 | Burger et al. | 514/456 |
| 5,157,132 A | 10/1992 | Tan et al. | 549/413 |
| 5,318,993 A | 6/1994 | Pearce | 514/690 |
| 5,348,974 A | 9/1994 | Wright et al. | 514/456 |
| 5,393,776 A | 2/1995 | Pearce | 514/486 |
| 5,602,184 A | 2/1997 | Myers et al. | 514/739 |
| 5,660,691 A | 8/1997 | Barnicki et al. | 203/72 |
| 5,663,461 A | 9/1997 | Mori et al. | 568/886 |
| 5,670,668 A | 9/1997 | Hyatt | 549/410 |
| 5,756,109 A | 5/1998 | Burger et al. | 424/401 |
| 5,919,818 A | 7/1999 | Lane et al. | 514/458 |

FOREIGN PATENT DOCUMENTS

| | | |
|---|---|---|
| EP | 0421419 A3 | 4/1991 |
| EP | 0421419 A2 | 4/1991 |
| EP | 0711749 A1 | 5/1996 |
| EP | 0711749 B1 | 5/1998 |
| JP | 63096155 A | 4/1988 |
| JP | 63250315 A | 10/1988 |
| JP | 07188119 A | 7/1995 |
| JP | 08133999 A | 5/1996 |
| JP | 09238692 A | 9/1997 |
| JP | 10025226 A | 1/1998 |
| JP | 10087480 A | 4/1998 |
| JP | 11130670 A | 5/1999 |
| WO | WO9938860 | 8/1999 |
| WO | WO9966929 | 12/1999 |

OTHER PUBLICATIONS

Pearce, B. C., et al., "Hypocholesterolemic Activity of Synthetic and Natural Tocotrienols," *J. Med. Chem.*, 35(20):3595–606 (Oct. 2, 1992).

Jondiko, I. J. O. and Pattenden, G., "Terpenoids and an Apocarotenoid from Seeds of *Bixa Orellana*," *Phytochemistry*, 28(11):3159–3162 (1989).

"Amazing Grain, How Sweet It Is," *Harvard Health Letter*, pp. 6–7 (Mar. 1997).

Theriault, A., et al., "Tocotrienol: A Review of Its Therapeutic Potential," *Clinical Biochemistry*, 32(5):309–319 (1999).

Yu, W., et al., "Induction of Apoptosis in Human Breast Cancer Cells by Tocopherols and Tocotrienols," *Nutrition and Cancer*, 33(1):26–32 (1999).

He, L., et al., "Isoprenoids Suppress the Growth of Murine B16 melanomas In Vitro and In Vivo," *American Society for Nutritional Sciences*, pp. 668–674 (1997).

Watkins, T. R. and Bierenbaum, M. L., "Tocotrienols: Biological and Health Effects," in *Antioxidant Status, Diet, Nutrition, and Health*, Andreas M. Papas, ed. (CRC Press) pp. 479–496 (1999).

"The Role of Annatto in Food Colouring," *Food Ingredients & Processing International*, pp. 23–27 (Feb. 1992).

Craveiro, A. A., et al., "The Presence of Geranylgeraniol in *Bixa Orelana* Linn.," *Quimica Nova*, 12(3):297–298 (1989).

Frega, N., et al., "Identification and Estimation of Tocotrienols in the Annatto Lipid Fraction by Gas Chromatography–Mass Spectrometry," *JAOCS*, 75(12):1723–1727 (1998).

Hyman, E. L., et al., "Reorienting Export Production to Benefit Rural Producers: Annatto Processing in Peru," *Journal of Rural Studies*, 6(1):85–101 (1990).

Chao, R.R., et al., "Supercritical $CO_2$ Extraction of Annatto (*Bixa orellana*) Pigments and Some Characteristics of the Color Extracts," *Journal of Food Science*, 56(1):80–83 (1991).

*Primary Examiner*—A Owens
(74) *Attorney, Agent, or Firm*—Hamilton, Brook, Smith & Reynolds, P.C.

(57) ABSTRACT

A source of material known as a byproduct solution of *Bixa orellana* seed components, which is obtained as an oily material after the bulk of annatto color, is removed from either the aqueous extract or solvent extract of annatto seeds. Further, this byproduct contains a tocotrienol component and a geranylgeraniol component and can be used as a source for the recovery of a tocotrienol component and a geranylgeraniol component.

31 Claims, 1 Drawing Sheet

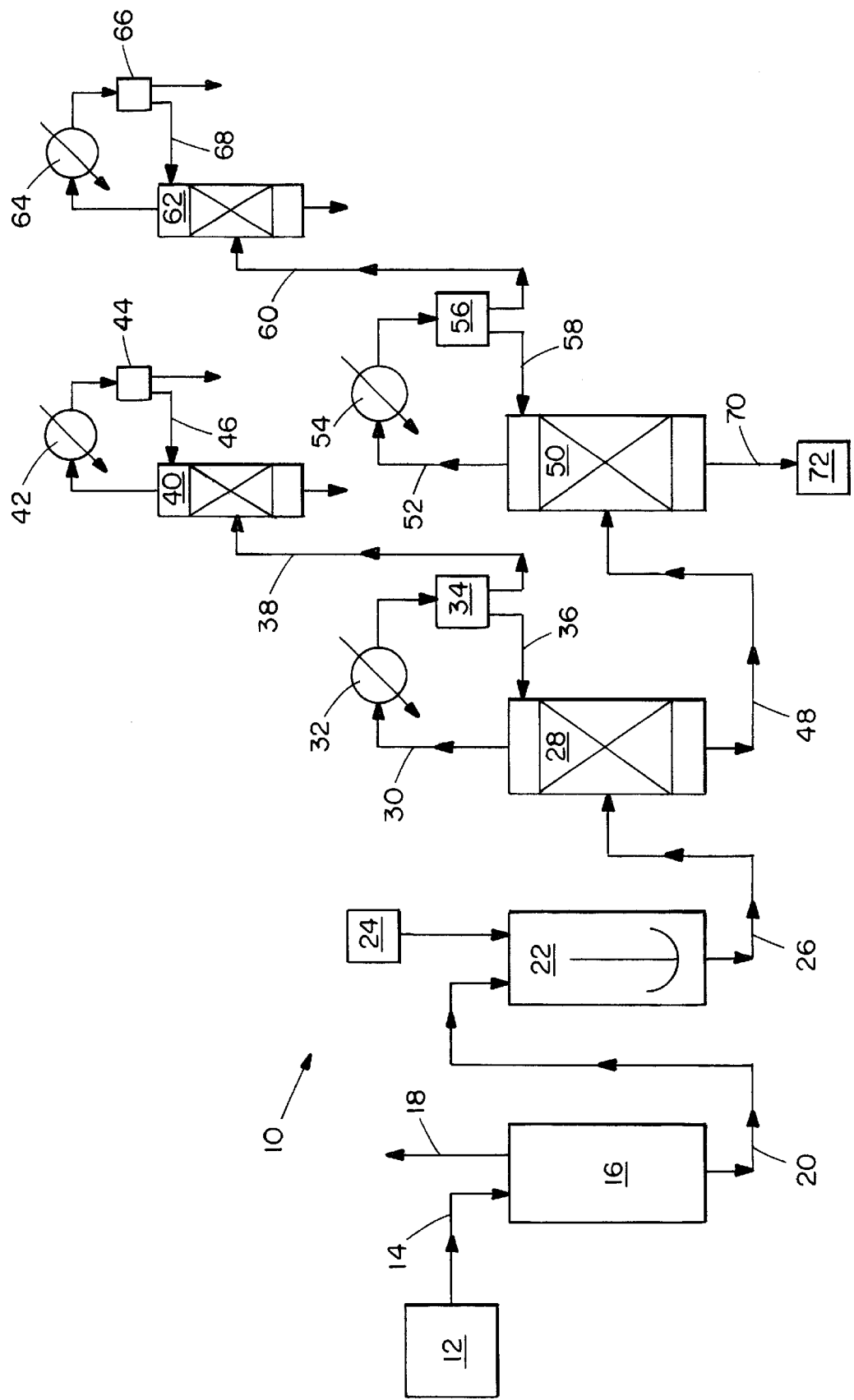

TOCOTRIENOLS AND GERANYLGERANIOL FROM *BIXA ORELLANA* BYPRODUCTS

RELATED APPLICATION

This application claims the benefit of U.S. Ser. No. 60/135,463, which was filed on May 24, 1999, the entire teachings of which are incorporated herein by reference.

BACKGROUND OF THE INVENTION

Tocotrienols generally are classified as farsnesylated chromanols (FC) and mixed terpenoids. Tocopherol and tocotrienol are believed to have beneficial effects because they act as antioxidants. Tocotrienols, in particular, have been documented to possess hypocholesterolemic effects as well as an ability to reduce atherogenic apolipoprotein B and lipoprotein plasma levels. Further, tocotrienols are believed to be useful in the treatment of cardiovascular disease and cancer. See, for example, Theriault, A., et al., "Tocotrienol: A Review of its Therapeutic Potential," *Clinical Biochemistry*, 32:309–319 (July 1999); and "Tocotrienols: Biological and Health Effects," in *Antioxidant Status, Diet, Nutrition, and Health*, Pappas, ed. (CRC Press), pp. 479–496 (1999). δ-tocotrienol and γ-tocotrienol, in particular, have been identified as effective suppressants of cholesterol activity, Qureshi, et al., "Response of Hypercholesterolemic Subjects to Administration of Tocotrienols," *Lipids*, 30(12) (1995), and in inducing apoptosis of breast cancer cells, Yu, et al., "Induction of Apoptosis in Human Breast Cancer Cells by Tocopherols and Tocotrienols," *Nutrition and Cancer*, 33(1):26–32 (1999).

Tocols, which includes tocopherols and tocotrienols, have several sources, including several vegetable oils, such as rice bran, soybean, sesame and palm oils. Tocotrienols have been discovered in the seeds of *Bixa orellana Linn*, otherwise known as the achiote tree. See, Jondiko, I.S., et al., "Terpenoids and an Apocarotenoid from Seeds of *Bixa Orellana*," *Phytochemistry*, 28(11):3159–3162 (1989). However, each source of tocotrienols and tocopherols generally contains more than a single tocol homolog. For example, palm oil and rice bran oil generally include both tocotrienols and tocopherols. Further, α-tocopherol has been reported to attenuate certain effects of tocotrienols, such as the cholesterol-suppressive activity of γ-tocotrienol. See, for example, Qureshi, et al., supra. In addition, because of their structural similarity, tocotrienols and tocopherols can be difficult to separate.

Geranylgeraniol includes acyclic diterpene alcohols (ADA) and geranylgeraniated terpenoids (GGT), and occurs naturally in linseed oil and cedrela toona wood and tomato fruit. Geranylgeraniol also has been discovered to exist in the seeds of *Bixa orellana*. See Craveiro, et al., "The Presence of Geranylgeraniol in *Bixa Orellana Linn*," *Quimica Nova*, 12(3):297–298 (1989). Potential uses for geranylgeraniol include synthesis of co-enzyme $Q_{10}$, vitamin K and tocotrienols. It is believed to inhibit esterification of retinol into inactive retinyl esters and, therefore, may be used to improve skin desquamation and epidermal differentiation. See U.S. Pat. No. 5,756,109, issued to Burger, et al. on May 26, 1998. Geranylgeraniol has been employed in conjunction with HMG-CoA reductase inhibitors in treatment of elevated blood cholesterol. See WO 99/66929 by Scolnick, published Dec. 29, 1999. Geranylgeraniol also is suspected to be useful for treatment of human prostate cancer. See U.S. Pat. No. 5,602,184, issued to Myers, et al. on Feb. 11, 1997. As with isolation of specific tocotrienols, geranylgeraniol must be separated from terpenoid compounds having similar structures when derived from natural sources. Separation of geranylgeraniol from these related compounds can be difficult.

Therefore, a need exists to find a method for recovery of δ- and γ-tocotrienols, and of geranylgeraniol, that minimizes or overcomes the above-referenced problems.

SUMMARY OF THE INVENTION

A source of material known as a byproduct solution of *Bixa orellana* seed components, which is obtained as an oily material after removing the bulk of annatto color, is removed from either the aqueous extract or solvent extract of annatto seeds. Further, this byproduct contains a tocotrienol component and a geranylgeraniol component and can be used as a source for the recovery of a tocotrienol component and a geranylgeraniol component.

The present invention generally is directed to a method of forming a tocotrienol composition.

The method includes volatilizing solvent from a byproduct solution of *Bixa orellana* seed components to form thereby a tocotrienol composition.

In one embodiment, the method further includes the step of distilling a geranylgeraniol component of the tocotrienol composition. At least a portion of the geranylgeraniol component is separated thereby from the tocotrienol composition to form a geranylgeraniol distillate.

In another embodiment, the method of forming a tocotrienol composition includes extracting at least a portion of an annatto component from *Bixa orellana* seeds, whereby an aqueous fraction is formed. The aqueous fraction includes the annatto component, a tocotrienol component and a geranylgeraniol component. The annatto component is precipitated from the aqueous fraction to form an annatto precipitate and a byproduct solution of *Bixa orellana* seed components. Water then is volatilized from the byproduct solution of *Bixa orellana* seed components to form the tocotrienol composition.

In still another embodiment, the method includes distilling tocotrienol components of the tocotrienol composition to form a tocotrienol distillate.

The present invention has many advantages. For example, the amount of δ-tocotrienol present in the byproduct solution of *Bixa orellana* seed components employed by the method is very high (500–700 times higher) relative to that found in other common sources, such as palm oil or rice bran oil. Further, and also in contrast to palm and rice bran oils, there is essentially no α-tocopherol present in the byproduct solution of *Bixa orellana* seed components employed by the method of the present invention. Therefore, the tocotrienol composition formed and, optionally, the tocotrienol distillate formed, generally does not require separation of δ-tocotrienol from α-tocopherol which, as discussed above, can have a mitigating effect on the therapeutic properties of δ-tocotrienol. Further, the byproduct solution of *Bixa orellana* seed components is a convenient source of geranylgeraniol. Therefore, relatively high concentrations of geranylgeraniol also can be obtained by the method of the invention.

BRIEF DESCRIPTION OF THE DRAWINGS

The FIGURE is a schematic representation of apparatus that can be employed to conduct the method of the invention.

DETAILED DESCRIPTION OF THE INVENTION

The features and other details of the invention, either as steps of the invention or as combinations of parts of the invention, now will be described more particularly and pointed out in the claims. It will be understood that the particular embodiments of the invention are shown by way of illustration and not as limitations of the invention. The principal features of the invention may be employed in various embodiments without departing from the scope of the invention.

*Bixa orellana Linn*, otherwise known as the achiote tree, is a member of the Bixaceae family and is native to tropical America. It is grown commercially in other parts of the world, generally within 20° of the equator or more preferably within 15° of the equator. The seeds of *Bixa orellana Linn* are the source of a reddish-orange colorant, known as annatto, that contains bixin and orelline, both of which are carotenoid pigments. The colorant is used commonly in foods, dyes and polishes. Typically, annatto is extracted from dehusked seeds in an aqueous caustic solution. The colorant is precipitated from aqueous caustic solution by addition of a suitable acid, such as sulfuric acid. The precipitated colorant is removed by filtration. Filtercake of precipitated annatto colorant is dried and milled to form a commercial product. An oily phase generally is separated from an aqueous caustic phase by centrifugation or by settling. Alternatively, the annatto colorant can be extracted from seeds in an organic solvent, such as hexane, acetone, or an alcohol. Miscella containing color and byproduct oil are allowed to cool sufficiently to precipitate the annatto colorant. The precipitate is separated as bottoms from the organic solvent. The oily phase from the caustic or organic extractions following separation of the annatto precipitate generally are discarded as byproducts.

It has been discovered that byproduct solutions of *Bixa orellana* seed components contain tocotrienols, including δ- and γ-tocotrienols, and geranylgeraniol. Further, it has been discovered that these materials are present in such solutions in very high quantities. For example, tocotrienols often can be present in an amount in a range of between about 10 percent and about 20 percent by weight. Geranylgeraniol often can be present in an amount in a range of between about 25 percent and about 80 percent by weight. In particular, it has been discovered that, surprisingly, tocotrienols and geranylgeraniol are present in the byproduct oily phase of annatto colorant from annatto seeds and, especially, from whole dehusked annatto seeds. Further, it has been discovered that large amounts of these non-saponifiable oily materials (e.g. tocotrienols and geranylgeraniol) can be extracted from a seed with only caustic water. Also, it has been discovered that tocotrienol-rich fractions and geranylgeraniol-rich fractions can be obtained in one unit of operation.

The method of the invention generally is directed to a method of forming a tocotrienol composition by volatilizing a solvent, such as water, or an organic solvent, from a byproduct solution of *Bixa orellana* seed components. A "byproduct solution of *Bixa orellana* seed components" is defined herein as a solution derived from *Bixa orellana* seed components having a concentration of annatto colorant significantly reduced from that of *Bixa orellana* seeds themselves. Other common terms for byproduct solution used for commercial products include: oil-soluble annatto color or annatto oil. Generally, the concentration of annatto colorant, which is defined as bixins and other carotenoids, chemically modified, altered or esterified, in byproduct solution of *Bixa orellana* seed is less than about two percent, by weight, such as between about 0.05 weight percent and about 2.0 weight percent.

A schematic representation of apparatus 10 suitable for conducting the method of the present invention is shown in FIG. 1. Byproduct solution of *Bixa orellana* seed components is directed from byproduct solution source 12 through line 14 to evaporator 16.

Materials of construction for use in apparatus 10, unless otherwise specified, include materials suitable for use with the process of the present invention. Examples of suitable materials of construction include glass and stainless steel. Methods of directing byproduct solution and fluid components thereof through apparatus 10 include, for example, pumping, such as with a positive-displacement pump or centrifugal pump, not shown, and application of pressure to the fluid source by directing a suitable non-reactive gas to the fluid source, such as nitrogen gas.

Solvent, such as water or an organic solvent, such as hexane, acetone or an alcohol, is volatilized from byproduct solution in evaporator 16 at a temperature and pressure sufficient to reduce the solvent content to a range of between about 0.05 weight percent and about 0.5 weight percent. Generally, solvent is volatilized at a temperature, and pressure sufficient to raise the concentration of tocotrienols to a range of between about 5 weight percent and about 20 weight percent. In one embodiment, water is volatilized in evaporator 16 at a temperature in a range of between about 20° C. and about 140° C. at an absolute pressure in a range of between about 10 torr and about 760 torr (all pressures are represented as absolute, rather than gauge pressures). Solvent volatilized from evaporator 16 is removed through conduit 18 and can be collected for reuse, such as in a subsequent extraction, or discarded. Volatilization of solvent from the byproduct solution forms a tocotrienol composition in evaporator 16.

The tocotrienol composition is directed from evaporator 16 through line 20 to vessel 22. Optionally, a suitable vegetable oil, such as rice bran oil, is directed into vessel 22 from vegetable oil source 24 and is mixed with the tocotrienol composition. The tocotrienol composition and vegetable oil are agitated in vessel 22. Addition of vegetable oil to the tocotrienol composition reduces viscosity of the tocotrienol composition and provides a more suitable medium for separating residual annatto colorant from the byproduct solution. In one embodiment, the amount of vegetable oil added to the tocotrienol composition is sufficient to cause the vegetable oil component of the tocotrienol composition to be in a range of between about 45 weight percent and about 30 weight percent.

The tocotrienol composition is directed from vessel 22 through line 26 to evaporator 28. Preferably, evaporator 28 is a thin film evaporator, such as a falling-film, wiped-film or short-path evaporator. The evaporator can be of a continuous mode or batch mode type. Geranylgeraniol is volatilized in evaporator 28 and removed as overhead vapor through line 30. The vapor is condensed in condenser 32 for recovery in vessel 34. Optionally, a portion of condensed distillate is returned to evaporator 28 as a reflux through line 36. In one embodiment, geranylgeraniol is distilled at a temperature in a range of between about 110 and about 210° C. at an absolute pressure below about 10 torr. Preferably, geranylgeraniol is distilled in evaporator 28 at a temperature below about 185° C. and at an absolute pressure below about 5 torr. Generally, distillation of geranylgeraniol is conducted for a sufficient period of time to reduce the concentration of geranylgeraniol in the tocotrienol composition in evaporator 28 to less than about 25 weight percent.

Recovered geranylgeraniol distillate in vessel 34 can be distilled further. Examples of suitable evaporators are the same as those described above for distillation of geranylgeraniol. In one embodiment, geranylgeraniol distillate is directed through line 38 to evaporator 40. In one embodiment, geranylgeraniol distillate is volatilized in evaporator 40 at a temperature in a range of between about 90° C. and about 220° C. and at a pressure in a range of between about 0.001 torr and about 5 torr. The vapor is condensed in condenser 42 and collected in receiver 44. A portion of the condensed distillate can be returned as reflux to evaporator 40 through line 46. Preferably, geranylgeraniol is distilled to obtain a concentration in receiver 44 in a range of between about 40 weight percent and about 80 weight percent.

The tocotrienol composition is directed from evaporator 28 through line 48 to evaporator 50 for distillation of tocotrienol. Suitable evaporators for distillation of tocotrienol include, for example, high vacuum wiped-film and short-path evaporators. Distillation can be conducted in a batch mode or continuous mode. In one embodiment, tocotrienol is distilled at a temperature less than about 250° C. Preferably tocotrienol is distilled in evaporator 50 at a pressure in a range of between about 0.001 torr and about 5 torr. Volatilized tocotrienol is directed through overhead line 52 and condensed in condenser 54 for collection in receiver 56. Condensed tocotrienol distillate can be directed back to evaporator 50 through reflux line 58. Generally, distillation of tocotrienol is conducted in a manner whereby the concentration of tocotrienol distillate in receiver 56 is in a range of between about 20 weight percent and about 50 weight percent.

Optionally, tocotrienol distillate in receiver 56 can be directed through line 60 to evaporator 62 for further distillation. Examples of suitable evaporators are the same as those described above for distillation of tocotrienols. In one embodiment, evaporator 62 is operated at a temperature in a range of between about 100° C. and about 250° C. and at a pressure in a range of between about 0.001 torr and about 5 torr. Distilled tocotrienol is condensed in condenser 64 and collected in receiver 66. Optionally, condensed tocotrienol distillate can be directed through reflux line 68 back to evaporator 62. Generally, the concentration of distilled tocotrienol in receiver 66 is in a range of between about 20 weight percent and about 90 weight percent.

Bottoms are collected from evaporator 50 through line 70 in receiver 72 and generally include residual annatto colorant. The bottoms can be processed by a suitable means to recover the colorant.

It is to be understood that, in an alternative embodiment, the geranylgeraniol and tocotrienol components can be distilled together, such as from a single vessel.

In an optional embodiment, byproduct solution of *Bixa orellana* seed components can be formed prior to, or in conjunction with, formation of the tocotrienol composition. For example, byproduct oil can be produced during the extraction of annatto seeds with either caustic water or a suitable solvent. In the caustic water process, annatto seeds are contracted with sufficient caustic water to remove most of the annatto color from the seeds. The bulk of the annatto color is separated from the aqueous extract as a solid. Byproduct oil is separated from the aqueous extract as a less dense than water phase either by centrifugation or settling. Optionally, water may be volatilized from the aqueous extract after the bulk of annatto color is removed to yield a byproduct oil.

In the solvent extraction method, annatto seeds are contacted with sufficient solvent to remove most of the annatto color from the seeds. The bulk of the annatto color is separated from the solvent as a solid. Byproduct oil is obtained following the removal of most of the solvent from the portion of the extract that is largely soluble after the separation of the bulk of the annatto color. Both caustic water extracted and solvent extracted byproducts contain tocotrienol and geranylgeraniol components that are useful to produce a tocotrienol composition and a geranylgeraniol composition.

Although the above methods are described for production of a suitable byproduct solution of *Bixa orellana* seed components, other methods can be employed. For example, the method described in Hyman, et al., "Reorienting Export Production to Benefit Rural Producers: Annatto Processing in Peru," *Journal of Rural Studies*, 6(1):85–101 (1990) is an example of a suitable method, the teachings of which are incorporated herein by reference in their entirety.

The invention now will be described further and specifically by the following Examples. All parts and percentages are by weight unless otherwise stated.

EXAMPLE 1

Annatto oil byproduct obtained from a commercial caustic extraction process was stripped of water in a rotary evaporator at 93° C. for 1.5 hours at about 50 torr. This removed 4 to 5 percent by volume of the material mostly as water. Rice bran oil was added so that the total volume of rice bran oil was 10 percent. This then was passed through a centrifugal high vacuum still operating at 90° C. at 2 to 5 torr. Less than 2 percent of the material distilled (odorous compounds and a small amount of water, all of which was discarded. Distillation continued and the conditions and amounts of distillates residues and tocotrienol and analysis are summarized below. Typical flow rates to the still were 1–21 per hour. Distillate and residues are reported as volume percent of material going to the centrifugal still.

GC conditions for GG analysis:
Column: 50 m capillary CB52 carbowax,
Detector: Flame ionization
50–220° C. at 10° C./minute. Hold at 220° C. for 9 minutes (total 26 minutes).
HPLC conditions for T3 analysis:
Column: Supelcosil LC Diol: 25 cm long, 3 mm I.D., 5 $\mu$m packing.
Mobile Phase: 97.5 Hexane:2.5 (2.5 Ethyl acetate:1.0 Acetic acid:0.1 Dimethoxypropane) 1.0 ml/min. (Isocratic)
Detector: Fluorescence 295 nm excitation, 340 nm emission.

Abbreviations used: tocotrienols (T3), geranylgeraniol (GG) natural color absorbance of a 1 percent solution in tetrahydrofuran at 428 nm (Abs), not analyzed (NA).

The material used for Pass 1 was a red oil with 15.7 percent T3 and an Abs of 37.0.

Pass 1: Distillation of GG at 120° C. and 0.03 torr

| Distillate: | 45% | T3 2.2% | GG 52% | Abs 0.65 |
|---|---|---|---|---|
| Residue: | 55% | T3 25.8% | | Abs 55.8 |

Residue of Pass 1 to Pass 2
Pass 2: Distillation of GG at 120° C. and 0.03 torr

| Distillate: | 22% | T3 4.2% | Abs NA |
|---|---|---|---|
| Residue: | 78% | T3 27.2% | Abs NA |

Residue of Pass 2 to Pass 3
Pass 3: Distillation of T3 at 198° C. and 0.01 torr

| Distillate: | 42% | T3 41.2% | Abs 3.7 |
| Residue: | 58% | T3 NA | Abs 79.5 |

Distillation of Pass 3 Distillate at 130 to 185° C. and about 0.01 torr produced fractions to more than 90 weight percent T3.

EXAMPLE 2

Byproduct annatto oil had a concentration of 17.9 percent tocotrienols after removal of low boiling compounds (10 percent water and odorous materials) on a wiped film evaporator at 120° C. and ca 20 torr. This was subjected to centrifugal high vacuum distillation as follows.
Pass 1: Distillation of GG at 130° C. and 0.08 torr

| Distillate: | 51% | T3 3.0% |
| Residue: | 49% | T3 28.5% |

Residue of Pass 1 was distilled after the addition of 18 percent rice bran oil in Pass 2.
Pass 2: Distillation of T3 and remaining GG at 210° C. and 0.08 torr

| Distillate: | 52% | T3 32.5% |
| Residue: | 48% | T3 7.9% |

EXAMPLE 3

Annatto oil byproduct obtained from a different manufacturer using the caustic extraction process of annatto seeds was processed in a manner similar to Example 1. After the removal water on a rotary evaporator ad the addition of 10 percent rice bran oil, this was subjected to centrifugal high vacuum distillation as follows:
Pass 1: Distillation of GG at 130° C. and 0.05 torr

| Distillate: | 43% | T3 2.4% | GG 56.7% |
| Residue: | 57% | T3 19.6% | |

Pass 2: Distillation of T3 and remaining GG at 200° C. and 0.05 torr

| Distillate: | 51% | T3 33.6% |
| Residue: | 49% | T3 5.4% |

Residue of Pass 2 to Pass 3
Distillation of Pass 2 distillate at 130 to 185° C. and about 0.01 torr produced fractions with up to 55 percent T3. Original material used for Pass 1 was 12.9 percent T3.

EXAMPLE 4

Annatto oil byproduct obtained from the commercial solvent extraction of annatto seeds was processed in a manner similar to Example 1. After the removal of most of the residual solvent on a rotary evaporator (5 percent), this material was subjected to centrifugal high vacuum distillation as follows:
Pass 1: Distillation of GG at 125° C. and 0.05 torr

| Distillate: | 45% | T3 2.5% | GG 45% |
| Residue: | 55% | T3 NA | |

10 percent rice bran oil was added to the Residue Pass 1, and distillation was continued.
Pass 2: Distillation of T3 and remaining GG at 205° C. and 0.09 torr

| Distillate: | 68% | T3 26.3% |
| Residue: | 32% | T3 6.3% |

Residue of Pass 2 to Pass 3
Pass 3: Distillation of GG at 115° C. and 0.08 torr

| Distillate: | 33% | T3 1.5% |
| Residue: | 67% | T3 34.5% |

Original material used for Pass 1 was 12.6 percent T3.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of forming a tocotrienol composition, comprising the step of volatilizing a solvent from a byproduct solution of *Bixa orellana* seed components to form thereby said tocotrienol composition.

2. The method of claim 1, wherein the solvent includes water.

3. The method of claim 1, wherein the solvent includes hexane.

4. The method of claim 1, wherein the solvent includes acetone.

5. The method of claim 1, wherein the solvent includes an alcohol.

6. The method of claim 1, therein the byproduct solution of *Bixa orellana* seed components includes a geranylgeraniol component.

7. The method of claim 1, further including the step of distilling the geranylgeraniol component to separate thereby at least a portion of said geranylgeraniol component from said tocotrienol composition to form a geranylgeraniol distillate.

8. The method of claim 7, further including the step of combining said byproduct solution with a vegetable oil.

9. The method of claim 8, wherein said vegetable oil includes rice bran oil.

10. The method of claim 7, further including the step of distilling a tocotrienol component of said tocotrienol composition to form a tocotrienol distillate and a bottoms stream.

11. The method of claim 10, wherein water is volatilized from the byproduct solution of *Bixa orellana* seed components by maintaining said solution at a temperature in a range of between about 20° C. and about 150° C. and at an absolute pressure in a range of between about 5 torr and about 760 torr.

12. The method of claim 11, wherein said water is volatilized from the byproduct solution for a period of time sufficient to reduce the water content of the tocotrienol composition to less than about 0.5 weight percent.

13. The method of claim 12, wherein the geranylgeraniol is distilled by maintaining the tocotrienol composition at a temperature in a range of between about 90° C. and about 220° C. and at an absolute pressure in a range of between about 0.001 torr and about 5 torr.

14. The method of claim 13, wherein the geranylgeraniol is distilled for a period of time sufficient to cause the geranylgeraniol component of the tocotrienol composition to be less than about 25 weight percent.

15. The method of claim 14, wherein the tocotrienol component is distilled by maintaining the tocotrienol composition at a temperature in a range of between about 140° C. and about 250° C. and at an absolute pressure in a range of between about 0.001 torr and about 5 torr.

16. The method of claim 15, wherein the tocotrienol component is distilled for a period of time sufficient to cause the tocotrienol content of the bottoms stream to be less than about 8 weight percent.

17. The method of claim 16, further including the step of distilling said geranylgeraniol distillate.

18. The method of claim 17, wherein said geranylgeraniol distillate is distilled by maintaining said distillate at a temperature in a range of between about 80° C. and about 220° C. and at an absolute pressure in a range of between about 0.001 torr and about 5 torr.

19. The method of claim 18, wherein said geranylgeraniol distillate is distilled under conditions sufficient to cause the geranylgeraniol concentration of said distillate to be greater than about 40 percent by weight.

20. The method of claim 16, further including the step of distilling said tocotrienol distillate.

21. The method of claim 20, wherein said tocotrienol distillate is distilled by maintaining said distillate at a temperature in a range of between about 100° C. and about 250° C. and at an absolute pressure in a range of between about 0.001 torr and about 5 torr.

22. The method of claim 21, wherein said tocotrienol distillate is distilled under conditions sufficient to cause the concentration of the tocotrienol distillate to be greater than about 25 percent by weight.

23. The method of claim 1, further including the step of forming the solution of *Bixa orellana* seed components.

24. The method of claim 14, wherein the geranylgeraniol is distilled by batch distillation of the tocotrienol composition.

25. The method of claim 24, further including the step of distilling further the distilled geranylgeraniol.

26. The method of claim 14, wherein the geranylgeraniol is distilled by continuous distillation of the tocotrienol composition.

27. The method of claim 26, wherein the continuous distillation includes a reflux of the distilled geranylgeraniol.

28. The method of claim 15, wherein the tocotrienol components are distilled by batch distillation of the tocotrienol composition.

29. The method of claim 28, further including the step of distilling further the distilled tocotrienol component.

30. The method of claim 29, wherein the tocotrienol component is distilled by continuous distillation of the tocotrienol composition.

31. The method of claim 30, wherein the continuous distillation includes a reflux of the distilled tocotrienol component.

* * * * *